United States Patent [19]

Myers

[11] Patent Number: 4,709,575
[45] Date of Patent: Dec. 1, 1987

[54] FLUIDIC OXYGEN SENSOR MONITOR

[75] Inventor: William P. Myers, Rock Island, Ill.

[73] Assignee: Litton Systems, Inc., Davenport, Iowa

[21] Appl. No.: 859,382

[22] Filed: May 5, 1986

[51] Int. Cl.$^4$ ............................................. G01N 7/00
[52] U.S. Cl. ............................................................ 73/23
[58] Field of Search ............................................... 73/23

[56] References Cited

U.S. PATENT DOCUMENTS

| | | | |
|---|---|---|---|
| 3,334,513 | 8/1967 | Thomas | 73/23 |
| 3,771,348 | 11/1973 | Villarroel | 73/23 |
| 3,817,085 | 6/1974 | Stubbs | 73/23 |
| 4,008,601 | 2/1977 | Woods | 73/23 |
| 4,100,789 | 7/1978 | Joyce | 73/23 |
| 4,341,108 | 7/1982 | Warncke et al. | 73/23 |
| 4,407,153 | 10/1983 | Furlong et al. | 73/23 |

FOREIGN PATENT DOCUMENTS 724985  3/1980  U.S.S.R. .................................. 73/23

Primary Examiner—Stewart J. Levy
Assistant Examiner—Joseph W. Roskos
Attorney, Agent, or Firm—Brian L. Ribando

[57] ABSTRACT

A fluidic bridge for determining the partial pressure of a gas has a positive pressure inlet for a reference gas and a sample gas and an ambient pressure outlet. The reference gas and the sample gas pass through a capillary passage and an orifice passage, and the pressure differential between the outlet of the reference capillary passage and the outlet of the sample capillary passage is a function of the density of the gas. A pressure ratio regulator is used to equalize the pressure of the reference gas and the sample gas applied to the inlets of the capillary passages. The length of the capillary passages and the flow characteristics of the orifice passages are adjustable to allow the bridge to be properly calibrated after being assembled.

12 Claims, 7 Drawing Figures

Fig_1
Prior Art

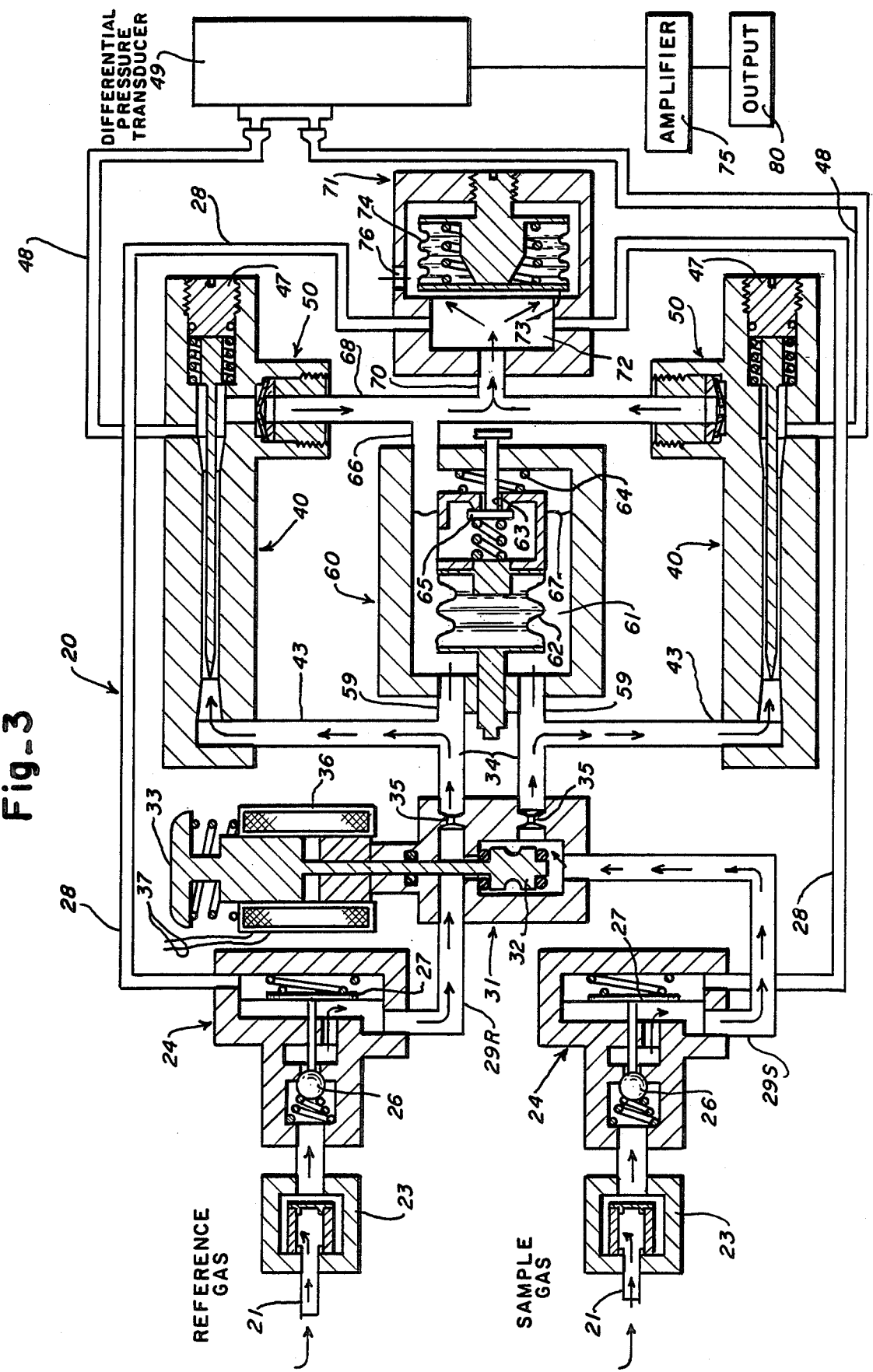

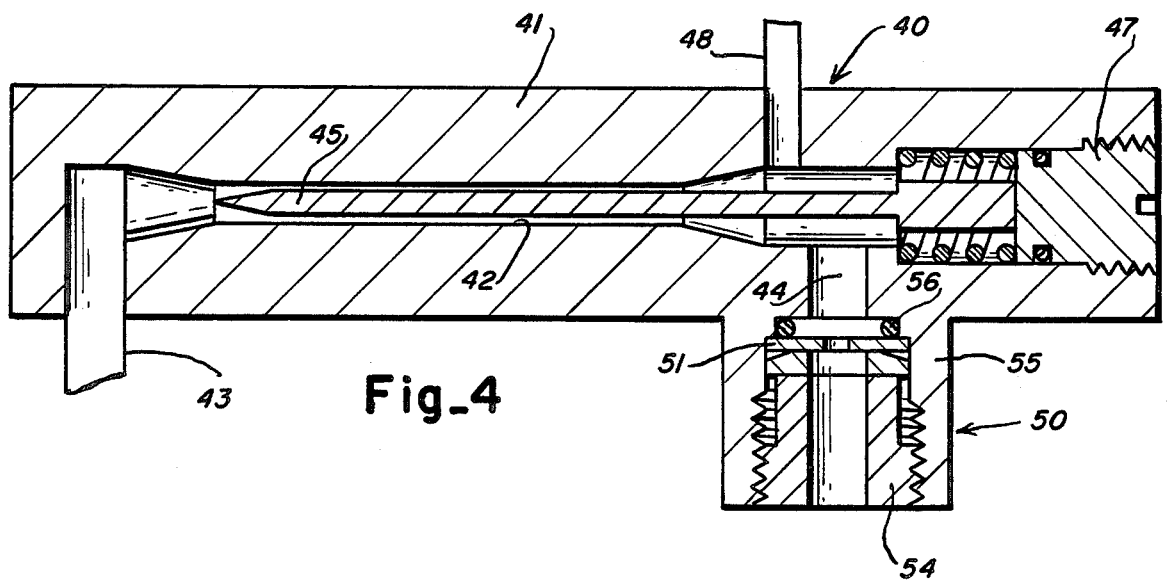
Fig_4
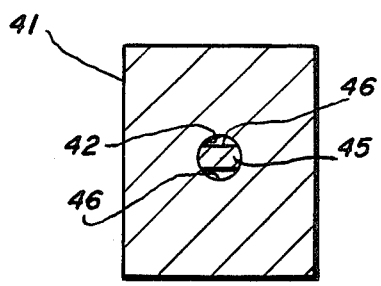
Fig_4A
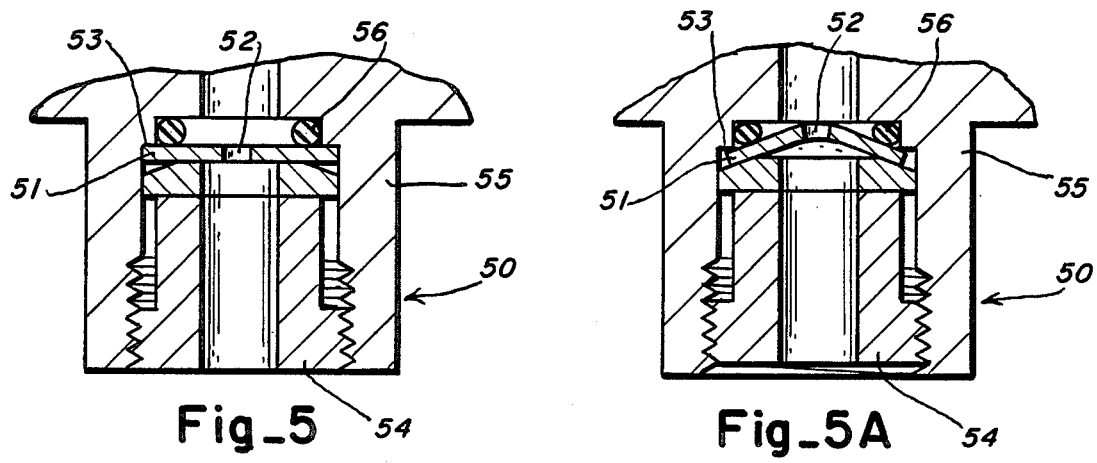
Fig_5
Fig_5A

FLUIDIC OXYGEN SENSOR MONITOR

BACKGROUND OF THE INVENTION

This invention relates to a fluidic oxygen sensor which is used to monitor the oxygen concentration of a sample gas.

The oxygen concentration of a sample gas can be determined by flowing a reference gas and the sample gas across a fluidic bridge and measuring the pressure differential in the two channels of the bridge caused by the two gases. Such a device is disclosed in U.S. Pat. No. 4,008,601 issued to Woods.

As further described in the Woods patent, the oxygen concentration of a sample gas can be monitored with a fluidic bridge consisting of two nonlinear orifice resistors and two linear capillary resistors. Sample gas containing oxygen flows through one channel of the bridge consisting of a capillary and orifice, and a reference gas flows through the second channel consisting of a similar capillary and orifice. If the two gases are at identical pressures at the inlet and at the outlet of the bridge, the pressure differential between the two channels at the midpoint between the capillaries and the orifices is a function of the difference in the viscosity and density of the sample and reference gases. If the pressure drop across the entire bridge is proportional to ambient pressure, the bridge differential pressure will be a function of the partial pressure of oxygen in the sample gas.

One of the major problems encountered in the use of a fluidic bridge of the prior art is assuring that the pressures of the sample and reference gases at the inlet and outlet of the bridge are identical. The customary method of providing identical inlet pressures as shown in the Woods patent is to vent the inlet to ambient pressure. Identical outlet pressures are assured by ejecting the sample and reference gases from the bridge with a jet pump. Since the bridge pressure drop must be a function of ambient pressure in order to sense the partial pressure of oxygen, the supply pressure to the jet pump must be controlled by a schedule pressure regulator to provide the desired pressure curve.

The prior art fluidic oxygen sensor as described above has several disadvantages. Since both the capillary and orifice resistors are fixed, calibration of the system is accomplished by adjustable needle valves in the inlet or outlet of each channel. These valves introduce degradation factors which reduce the sensitivity of the sensor. The jet pump which is used to eject the gases from the bridge consumes a supply of forced air. Pressure drop across the bridge caused by the jet pump is difficult to control and is subject to variations caused by altitude and temperature changes. Since the inlet pressure is limited to available ambient pressure, at high altitudes it is difficult to obtain a linear signal readout because of the limited pressure differential. Finally, it is difficult to filter and sample the reference gases at the inlet of the bridge without disturbing the ambient pressure level since after a period of operation the filter in each line begins to clog which increases the pressure drop across each filter to an unknown value.

SUMMARY AND OBJECTS OF THE INVENTION

According to the invention, the inlet of a fluidic bridge is maintained at positive pressure and the outlet is at ambient pressure in order to obviate the disadvantages of the prior art. A pressure ratio regulator maintains the same positive inlet pressure for both the sample gas and the reference gas which is proportional to altitude pressure. Since in each channel the capillary must be matched with the orifice in order to obtain an accurate and sensitive bridge system, at least one of these elements in each channel is adjustable so that the system may be fine tuned after assembly.

It is accordingly an object of the invention to provide a fluidic bridge for monitoring the partial pressure of a gas wherein the inlets of the bridge are maintained at a positive pressure and the outlet is at ambient pressure.

It is another object of the invention to provide a fluidic bridge including an inlet pressure ratio regulator which maintains an equalized positive inlet pressure for both a sample gas and a reference gas.

It is another object of the invention to provide a fluidic bridge including adjustable capillary and orifice elements whereby the bridge can be adjusted after assembly for optimum performance.

These and other objects of the invention will be apparent from the following detailed description in which reference numerals used throughout the description designate like or corresponding parts on the drawings.

BRIEF DESCRIPTION OF THE DRAWINGS

FIG. 3 shows the elements which comprise the fluidic bridge of FIG. 2.

FIGS. 4 and 4A are detail views of an adjustable capillary used in the fluidic bridge of FIGS. 2 and 3.

FIGS. 5 and 5A are detail views of the adjustable orifices used in the fluidic bridge of FIGS. 2 and 3.

DESCRIPTION OF THE PRIOR ART

Figure 1:
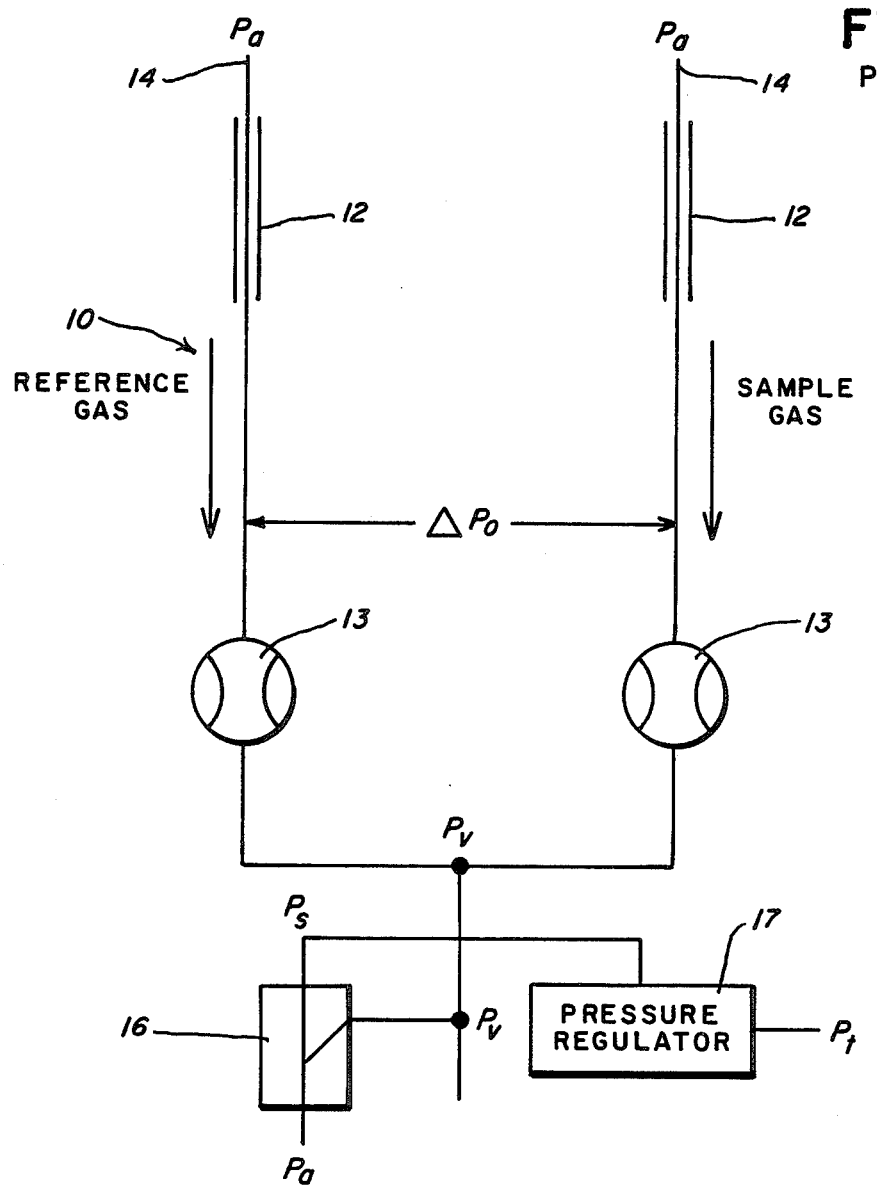
FIG. 1 shows a fluidic bridge according to the prior art.

FIG. 1 shows a simplified fluidic bridge circuit of the prior art. The bridge circuit 10 comprises two series combinations of a capillary resistor 12 and an orifice resistor 13 which are in parallel channels. A reference gas flows through one channel and a sample gas flows through the other channel. The inlet 14 of each series combination is at ambient pressure $P_a$, and the outlet of the bridge circuit and the inlet of jet pump 16 is at pressure $P_v$ which is less than $P_a$. The jet pump 16 is coupled to a pressure regulator 17 which supplies a gas flow at pressure $P_s$ to the pump to extract the gas from the bridge circuit 10. The outlet of the jet pump 16 is at ambient pressure $P_a$.

In operation, the pressure differential $\Delta P_o$ between the two channels which is measured at the midpoint between the capillaries 12 and the orifices 13 will be dependent on the difference in the viscosity and the density of the sample and the reference gases.

DESCRIPTION OF THE PREFERRED EMBODIMENT

Figure 2:
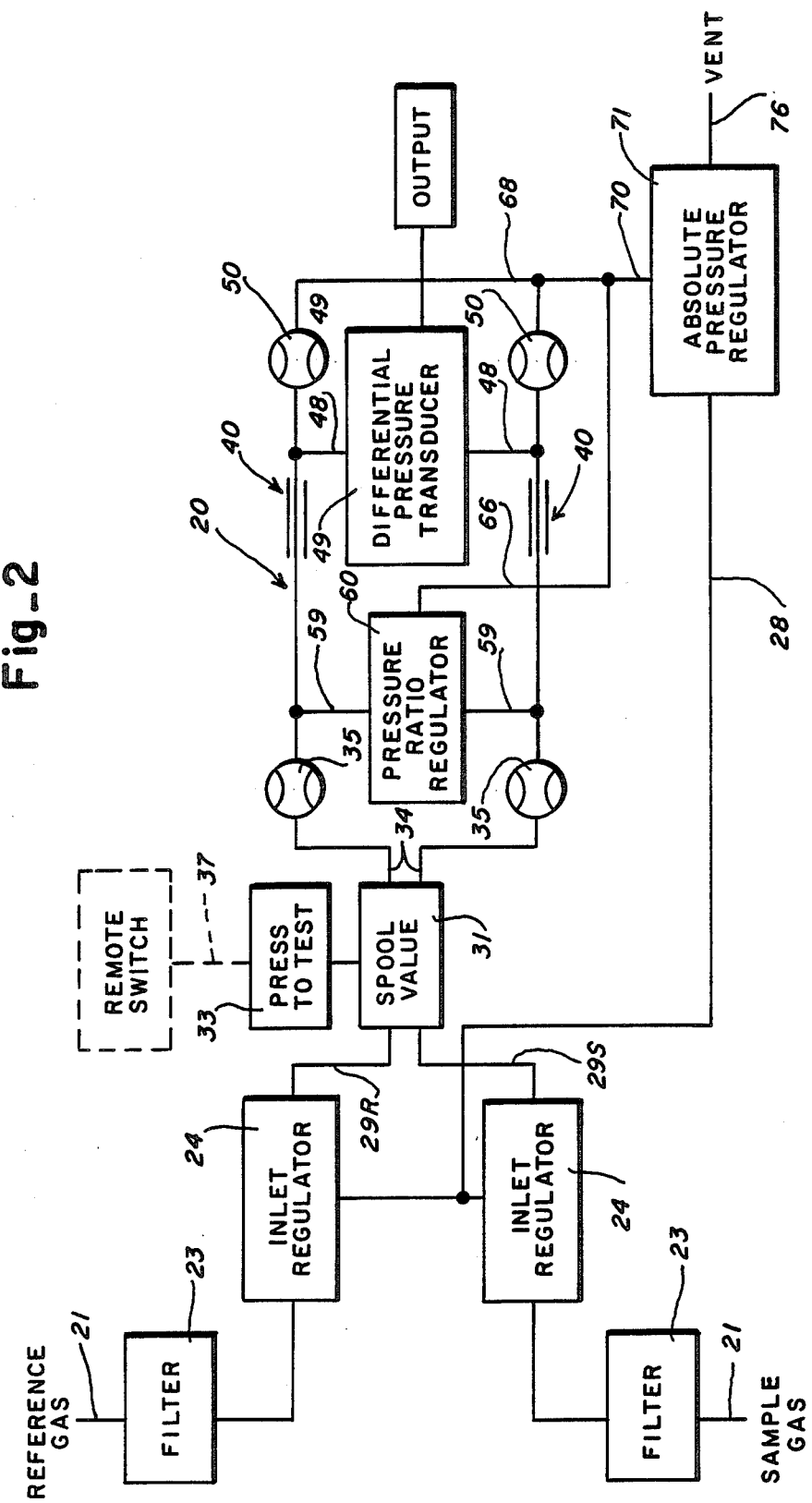
FIG. 2 is a schematic representation of a fluidic bridge according to the invention.

FIGS. 2 and 3 show the fluidic sensor 20 according to the present invention. Both the reference gas and the sample gas enter the fluidic sensor 20 under pressure by means of a positive pressure inlet 21. The pressure source for pressurizing the reference gas and the sample gas may be of conventional design and does not form a part of the present invention. However, the use of the positive pressure inlet 21 results in a fluidic sensor having a mode of operation which is distinct from the fluidic sensors of the prior art. Each positive pressure inlet 21 is coupled to a filter element 23 which filters any particulate material from the incoming reference gas and sample gas. Each filter element 23 is coupled to an inlet pressure regulator 24. The inlet pressure regulator comprises a valve element 26 which is controlled by a spring loaded diaphragm 27. The diaphragm 27 is responsive to a downstream control pressure which is coupled to the diaphragm by a control passage 28. The control pressure plus the spring force regulates the valve 26 allowing incoming gas to enter the system.

The outlets 29R and 29S of the inlet pressure regulators 24 are coupled to a spool valve 31. The spool valve 31 includes a spool element 32 which in the position shown allows gas from outlets 29R and 29S to pass through the spool valve 31 to either side of the fluidic sensor 20. A press-to-test button 33 is coupled to the spool element 32. Pressure on the press-to-test button 33 causes the spool element 32 to block the gas flow from the outlet 29S and to admit gas from outlet 29R to both outlets 34 of the spool valve 31. The press-to-test button may be actuated remotely by means of a solenoid 36 which is coupled by leads 37 to a remote switch. The outlet 34 of the spool valve 31 each include a flow restrictor 35. Each spool valve outlet 34 is coupled to the inlet 43 of an adjustable capillary 40 and to a pressure ratio regulator 60.

The dimensional accuracy of the laminar flow capillaries 40 and of the turbulent flow orifices 50 which are downstream of the capillaries 40 are important in determining the accuracy and sensitivity of the sensor. The pressure drop across the capillaries 40 is sensitive to the viscosity of the gas, and the pressure drop across the orifices 50 is sensitive to the density of the gas. Since in each channel the capillaries and orifices must be matched to one another, one or both of these elements in each channel is adjustable.

The capillaries 40 consist of an elongated body 41 with a burnished bore 42 and a polished pin 45 that is sized for a slip fit into the bore as shown in FIG. 4A. The slip fit assures that there is no movement of the pin 45 relative to the bore 42 caused by shock and vibration which could result in a shaft in calibration. Flats 46 are ground on the sides of the pins 45 to provide capillary flow passages with circular segment shaped cross sections. The ends of the bore 42 and pin 45 are tapered to minimize nonlinear resistance caused by turbulence at the inlet 43 and outlet 44 of the capillary. The linear resistance (pressure drop) of the capillary is varied by adjusting the length of pin engagement in the bore with a screw 47. Precise linear flow resistances for the gas can be obtained by these adjustments without expensive production techniques which would otherwise be needed to maintain identical dimensions and surface finishes on the capillary elements.

The downstream end of each capillary bore 42 is coupled by passage 48 to a differential pressure transducer 49.

The outlet 44 of each adjustable capillary 40 is coupled to an adjustable orifice 50 as best shown in FIGS. 5 and 5A. The adjustable orifice comprises a housing 55 and a spring steel disc 51 having a bore 52 therethrough. The disc is positioned within the housing on a shoulder 53 and is biased against the shoulder by a hollow screw 54. An o-ring 56 provides a seal between the disc 51 and the housing 55.

The dimensional accuracy of the bridge orifice bores 52 is even more critical than the capillaries 40. Calculations show that uncompensated orifice dimensional variations of plus or minus five millionths of an inch cause unacceptable inaccuracies in the bridge output. In the prior art, if a fixed orifice bore is sized manually with a burnishing tool and is sized too large, it is necessary to disassemble the bridge and replace the orifice. According to the invention and as shown in FIG. 5A, the adjustable spring steel disk 51 can be flexed by tightening the hollow screw 54 to reduce the flow area through the bore 52. If reverse adjustment is required, the flexing force on the disk is lessened and the disk flattens to increase the flow area.

In actual practice, it has been found that a capillary and an orifice in a series combination can be matched by adjustment of the capillary alone. Accordingly, in some embodiments it may be desirable to provide an adjustable capillary and a fixed orifice.

With reference again to FIGS. 2 and 3, the outlets 34 of the spool valve 31 are additionally coupled to two inlets 59 of a pressure ratio regulator 60 which maintains the same positive inlet pressure for both the reference gas and the sample gas that is proportional to altitude pressure. The pressure ratio regulator 60 comprises a common pressure chamber 61, and an evacuated bellows capsule 62 which is coupled to a port element 62 which is supported by a diaphragm 67. The port 63 is biased by a spring 64 and a valve 65 is positioned to control flow through the port 63 and to the regulator outlet 66. The pressure ratio regulator outlet 66 is combined with the outlets 68 from the adjustable orifices 50 and is coupled to the inlet 70 of an absolute pressure regulator 71.

The absolute pressure regulator 71 comprises a regulator chamber 72 which is normally vented to ambient pressure through the regulator outlet 76. The pressure in the regulator chamber 72 is coupled by means of the feedback passages 28 to the diaphragms 27 in the inlet pressure regulators 24. A valve 73 in the regulator chamber 72 is actuated by a spring loaded aneroid 74 to close the regulator chamber 72 from ambient pressure at a preselected altitude.

MODE OF OPERATION OF THE PREFERRED EMBODIMENT

In the mode of operation which is disclosed below, although reference will often be had to only one channel of the fluidic sensor, it will be understood that unless otherwise indicated, the description refers to both channels.

In the preferred embodiment, the invention is used to monitor the partial pressure of oxygen in a breathing gas which is delivered to a pilot, wherein the desired oxygen partial pressure is 220 mm Hg.

Pressurized gas enters the fluidic sensor via the positive pressure inlet 21 and is immediately filtered by the filter 23. The inlet pressure regulator 24 controls the flow rate of the gas in each channel by controlling the pressure drop across the flow restrictors 35. This insures that the input of both channels to the pressure ratio regulator is approximately balanced. Each inlet pressure regulator 24 is controlled as a function of ambient pressure by means of the feedback pressure passage 28.

The regulated gas from the flow restrictor 35 is coupled to the input of the adjustable capillary 40 and the pressure ratio regulator 60. Since both inlets 59 to the pressure ratio regulator 60 are coupled to the same pressure chamber 61, the pressure ratio regulator 60 insures that the pressure for both the reference gas and the sample gas across the bridge elements 40 and 50 is the same. The effective area of the diaphragm 67 is greater than the effective area of the bellows capsule 62 with the result that an increase in the pressure within the pressure chamber 61 will cause the port 63 to move away from the valve 65 thus opening the port 63. The reference and the sample gas flow to the inlet 43 of their respective adjustable capillaries 40. The capillaries 40 cause a pressure drop in the reference gas and the sample gas which is dependent upon the viscosity of the gas.

The downstream side of the adjustable capillary 40 is coupled to the differential pressure transducer 49. The differential pressure transducer 49 measures the differential pressure between the reference gas and the sample gas and provides an electrical signal to an amplifier 75. The amplifier 75 amplifies the signal and applies it to an output device which is calibrated to give an indication of the partial pressure of the sample gas. The reference and sample gases then pass through the respective adjustable orifices 50 and enter the pressure chamber 72 of the absolute pressure regulator 71. The gases are vented from the outlet 76 of the absolute pressure regulator 71 at ambient pressure.

The spool element 32 within the valve 31 provides a press-to-test function whereby a failure condition is impressed upon the oxygen monitor for test purposes. By actuating the press to test button 33, air, which has an oxygen partial pressure at sea level of approximately 160 mm. Hg., is applied to the sample gas side of the fluidic bridge. Assuming that an oxygen partial pressure of at least 180 mm. Hg. is desired, the differential pressure transducer 49 if operating properly will detect a low oxygen partial pressure condition and will actuate an alarm under the test conditions. Once this test has been made, the press-to-test button is released allowing both the reference gas and the sample gas to flow through the fluidic sensor.

The control passages 28 reference the inlet pressure regulators 24 to the pressure existing within the pressure chamber 72. Below a preselected altitude, the pressure chamber 72 is vented to ambient. Above the preselected altitude the aneroid 74 causes the valve 73 to close the vent path to ambient and to maintain the pressure in the chamber 72 at the preselected altitude pressure. Thus, above the preselected altitude, the inlet regulators 24 are referenced to the preselected altitude pressure. The purpose of this feature is to avoid a warning signal at high altitudes where a sample gas comprising as much as 94% oxygen will not provide an adequate oxygen partial pressure.

Having thus described the invention, various alterations and modifications thereof will become apparent to those skilled in the art, which alterations and modifications are intended to be within the scope of the invention as defined by the appended claims.

What is claimed is:

1. A fluidic sensor for determining the partial pressure of oxygen in a gas comprising:
   a positive pressure inlet for a reference gas and a positive pressure inlet for a sample gas,
   a capillary passage for the reference gas and a capillary passage for the sample gas,
   an orifice passage for the reference gas and an orifice passage for the sample gas,
   an outlet for the fluidic sensor at ambient pressure, and
   means coupled to the outlets of the capillary passages for detecting a pressure differential between the outlet of the reference capillary passage and the outlet of the sample capillary passage.

2. The fluidic sensor of claim 1 further comprising:
   means for equalizing the pressure of the reference gas and the sample gas applied to the inlets of the capillary passages.

3. The fluidic sensor of claim 2 wherein inlet pressure regulators control the pressure of the reference gas and the sample gas applied to the fluidic sensor.

4. The fluidic sensor of claim 2 wherein means are provided for varying the capillary length of the adjustable capillaries in order to match the linear resistance of the capillary to the nonlinear resistance of the orifice.

5. The fluidic sensor of claim 4 wherein the means for varying comprises an elongated needle positioned in a bore of the capillary body and wherein the position of the needle within the bore may be selectively varied to vary the capillary length.

6. The fluidic sensor of claim 5 wherein the elongated needle is dimensioned for a slip fit within said bore, and the capillary passages are formed between the sides of the bore and flats which are ground onto the surface of the elongated needle.

7. The fluidic sensor of claim 2 wherein the flow characteristics of the orifice passages are adjustable.

8. The fluidic sensor of claim 6 wherein the orifice passages comprise:
   an orifice through a flexible disc, and
   means for flexing said disc to alter the flow characteristics of said orifice.

9. The fluidic sensor of claim 2 wherein means are provided for coupling the reference gas to both adjustable capillaries in the fluidic sensor in order to test the operation of the sensor.

10. The fluidic sensor of claim 2 further comprising:
    a pressure ratio regulator, and
    a common pressure chamber in the pressure ratio regulator comprising the means for equalizing the pressure of the reference gas and the sample gas.

11. The fluidic sensor of claim 3 further comprising:
    an absolute pressure regulator,
    vent means for venting a regulator chamber of the absolute pressure regulator to ambient pressure, and
    feedback passages for coupling the regulator chamber to the inlet pressure regulators.

12. The fluidic sensor of claim 11 further comprising:
    aneroid means for controlling the vent means, whereby the regulator chamber is vented to ambient pressure below a preselected altitude, and the regulator chamber is sealed from ambient pressure above said preselected altitude.

* * * * *